United States Patent [19]

Marschner et al.

[11] 4,087,449
[45] May 2, 1978

[54] PROCESS FOR PRODUCING METHANOL

[75] Inventors: Friedemann Marschner, Weisskirchen; Emil Supp, Dietzenbach; Günter Pockrandt, Bad Homburg, all of Germany

[73] Assignee: Metallgesellschaft Aktiengesellschaft, Frankfurt am Main, Germany

[21] Appl. No.: 776,078

[22] Filed: Mar. 9, 1977

Related U.S. Application Data

[63] Continuation of Ser. No. 608,300, Aug. 27, 1975, abandoned.

[51] Int. Cl.$^2$ .............................................. C07C 29/16
[52] U.S. Cl. ................................. 260/449.5; 252/373
[58] Field of Search ...................................... 260/449.5

[56] References Cited

U.S. PATENT DOCUMENTS

| 2,276,343 | 3/1942 | Ryerson et al. | 252/373 |
|---|---|---|---|
| 3,763,205 | 10/1973 | Green | 260/449.5 |
| 3,897,471 | 7/1975 | Herbert et al. | 260/449.5 |
| 3,920,717 | 11/1975 | Marion | 260/449.5 |
| 3,972,958 | 8/1976 | Garwood | 260/449.5 |

FOREIGN PATENT DOCUMENTS

| 2,202,165 | 7/1973 | Germany | 252/373 |
|---|---|---|---|
| 1,164,407 | 9/1969 | United Kingdom | 252/373 |
| 1,169,241 | 10/1969 | United Kingdom | 260/449.5 |
| 1,190,071 | 4/1970 | United Kingdom | 260/449.5 |
| 1,262,479 | 2/1972 | United Kingdom | 260/449.5 |
| 1,309,872 | 3/1973 | United Kingdom | 260/449.5 |

OTHER PUBLICATIONS

Hiller et al., Chem. Economy & Eng. Review, Sep. 1971, pp. 14–15.
Feldman, Chemical Reaction Engineering Reviews, Adv. in Chemistry Series 148, Third Int. Symposium held at Evanston, Ill. Aug. 27–29, 1974, pp. 132–137, 142–143, 153–154.

*Primary Examiner*—Howard T. Mars
*Attorney, Agent, or Firm*—Burgess, Dinklage & Sprung

[57] ABSTRACT

A process for producing methanol wherein coal is gasified by a treatment with water vapor and oxygen at elevated temperature, the resulting gas is cooled and is scrubbed with an organic solvent to remove impurities from the gas, the carbon oxides contained in the gas are catalytically reacted with hydrogen to form methanol, and the methanol is separated, the improvement comprises subjecting the residual gas left after the separation of the methanol to a catalytic cracking treatment with water vapor under pressure and at elevated temperature to form hydrogen and carbon oxides and cooling the cracked gas and recycling it to the methanol synthesis.

1 Claim, 1 Drawing Figure

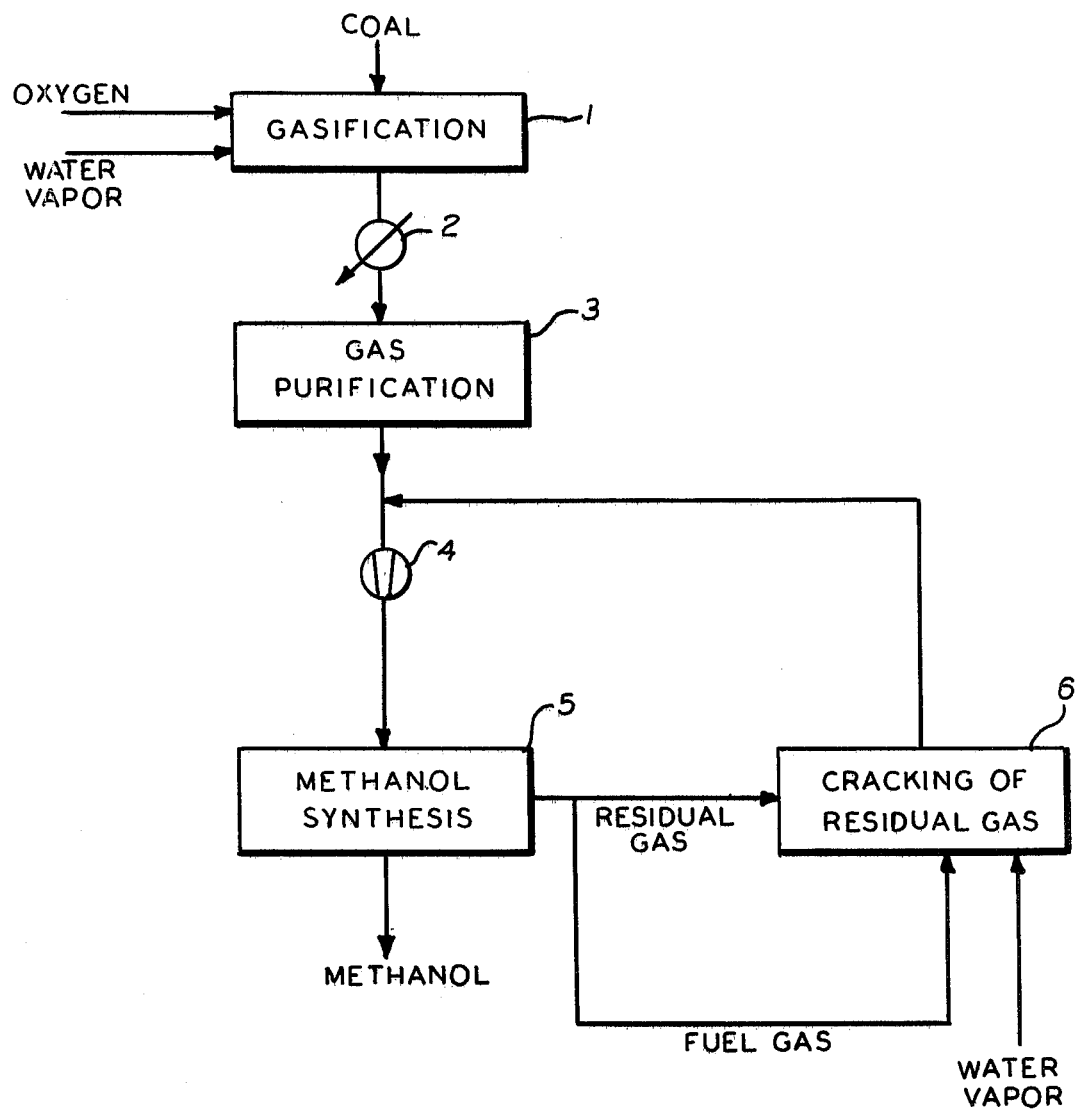

PROCESS FOR PRODUCING METHANOL

This is a continuation of application Ser. No. 608,300 filed Aug. 27, 1975, and now abandoned.

BACKGROUND

This invention relates to a process of producing methanol in which coal is gasified by a treatment with water vapor and oxygen at elevated temperature, the resulting gas is cooled and is scrubbed with an organic solvent to remove impurities from the gas, the carbon oxides contained in the gas are catalytically reacted with hydrogen to form methanol, and the methanol is separated.

Numerous processes of producing methanol are known. German Pat. No. 1,668,390 describes a process of producing methanol from a synthesis gas mixture which consists of $H_2$, CO, and $CO_2$ at copper-containing catalysts under pressures of 20–200 kg/cm$^2$, in which the heat of reaction is dissipated by a heat exchange with a liquid cooling fluid. The catalyst is arranged in layers having a height of at least 2 meters in tubes which are 20–80 mm in inside diameter and surrounded by a fluid which is kept at a temperature of 190–250° C, and the mass velocity of the synthesis gas is maintained at least 2000 kg/m$^2$-h.

According to another proposal the gas which contains CO, $CO_2$, and hydrogen is catalytically reacted under a pressure of 20–100 kg/cm$^2$ above atmospheric pressure and at a temperature of 200–300° C (Printed German Application 1,930,702). The synthesis gas has preferably a composition which meets the conditions $$XH_2 = 3\ XCO_2 + a\ XCO$$

and $$XCO_2 = b\ XCO$$

where $a$ is in the range of 2.5–8.0, preferably 3.0–4.5, and $b$ in the range of 0.1–1.0, preferably 0.2–0.4.

According to German Pat. No. 2,024,301, methanol is produced in that high-boiling hydrocarbons are partially oxidized by a treatment with oxygen and water vapor under a pressure which is at least 5 kg/cm$^2$ above the pressure of the methanol synthesis, the resulting raw gas is purified in one or more stages, and the resulting purified synthesis gas is reacted under a pressure of 30–80 kg/cm$^2$ (absolute pressure).

German Pat. No. 1,296,133 describes a further process in which a raw gas which consists mainly of hydrogen and carbon monoxide and has been produced in that solid or liquid fuels were gasified by a treatment with oxygen and water vapor is converted to a synthesis gas for the methanol synthesis, and in which the raw gas is optionally prepurified and subsequently entirely desulfurized and the carbon monoxide contained in a branch stream of the resulting gas is converted to hydrogen and carbon dioxide by a shift conversion treatment with water vapor. Said branch stream is controlled at such a rate that a gas which contains two parts of hydrogen and one part of carbon monoxide is obtained when the two branch streams are combined behind the shift conversion plant and the carbon dioxide is scrubbed from the mixed gas. The process is characterized in that the raw gas which has been cooled and is free of condensate, inclusive of water, and the mixed gas which has the proper $CO:H_2$ ratio as a result of the shift conversion of part of the carbon monoxide, are scrubbed in known manner with xylene at $-10°$ C to 30° C and under pressures of 10–150 kg/cm$^2$ (absolute pressure).

In this process and the other known processes, e.g., the process according to German Pat. No. 2,024,301, at least part of the preferably desulfurized raw gas is treated with water vapor to effect a shift conversion of the carbon monoxide contained in the gas into hydrogen and carbon dioxide.

This shift conversion is a catalytic reaction in which, e.g., iron oxide-chromium oxide catalysts are employed (see German Pat. No. 1,296,133). It involves additional labor costs and adds to the cost of the final product.

SUMMARY

This invention avoids these and other disadvantages and provides a new process which enables methanol to be produced in a simple and economical manner.

Specifically, it is possible to use even low-grade solid fuels for the production, such as coal of any desired origin and also coal which yields a large amount of methane when gasified.

This is accomplished according to the invention in that the residual gas left after the separation of the methanol is subjected to a catalytic cracking treatment with water vapor under pressure and at elevated temperature to form hydrogen and carbon oxides and the cracked gas is cooled and is recycled to the methanol synthesis.

According to a preferred feature of the process of the invention, the residual gas is cracked under a pressure of 5–50 bars, preferably 10–30 bars, and at a temperature of 500–900° C, preferably 700–850° C.

DESCRIPTION

The cooled cracked gas is desirably recycled into the pure gas.

According to another preferred feature of the invention the cooled cracked gas is recycled into the gas produced by the gasification of coal.

The advantages afforded by the invention reside particularly in that a simple and economically desirable process is provided by which methanol, which is valuable for numerous chemical synthesis, can be produced from inexpensive raw materials, such as coal. The starting products may include coals which usually are not employed for the synthesis of methanol, such as coals which yield a large amount of methane when gasified.

Whereas the methane evolved during the gasification of these coals can be cracked by a treatment with oxygen to form methanol, that method requires much energy and is highly expensive. Another important advantage of the process according to the invention is the fact that the shift conversion stage is eliminated so that the production of methanol is simplified and reduced in cost because the high capital investment for a shift conversion reactor, catalysts and the like is eliminated.

Because the coal which is fed is fully utilized, the end product is obtained with a high yield, which has not been attained in the conventional processes.

Conventional reactors, such as tubular reactors, can be used for the synthesis of the methanol. Such reactors have been described, e.g., in Printed German Application No. 2,153,437.

The invention is shown diagrammatically in the accompanying drawing by way of a flow diagram and will be described more fully in the following Example.

EXAMPLE

A coal was used which had the following composition in % by weight:
Carbon elemental — 55.64;

Carbonate carbon dioxide — 2.17;
Hydrogen — 4.42;
Sulfur — 5.63;
Sulfate sulfur — 0.13;
Nitrogen — 1.24;
Oxygen — 9.04;
Mineral constituents (oxides) — 9.70;
Total water — 12.03;
and a net calorific value of 5266 kcal/kg.

1000 kg of said coal were gasified in 1 by a treatment with 182 standard $m^3$ oxygen and 753 standard $m^3$ water vapor under a pressure of 30 bars and at a temperature of 1400° C with the coal moving in a counterflow to the gasifying agents. The raw gas obtained in an amount of 1428 standard $m^3$ had the following composition in % by volume:

$CO_2$ — 28.6;
CO — 13.7;
$H_2$ — 38.5;
$CH_4$ — 11.6;
$N_2$ — 0.2;
$H_2S$ + COS — 2.4;

The 1428 standard mraw gas were cooled to 40° C in a cooler 2 and the cooled gas was scrubbed in a gas purification stage with cold methanol at −40° C. The resulting 1003 standard $m^3$ pure gas had the following composition in % by volume:

$CO_2$ — 3.4;
CO — 26.2;
$H_2$ — 54.4;
$CH_4$ — 15.7;
$N_2$ — 0.3;
$H_2S$ + COS — 0.1 ppm.

According to the invention, 897 standard $m^3$ cracked gas from the residual gas cracking unit 6 were added to said pure gas to form 1900 standard $m^3$ methanol synthesis gas having the following composition in % by volume:

$CO_2$ — 6.7;
CO — 19.2;
$H_2$ — 63.4;
$CH_4$ — 10.1;
$N_2$ — 0.6.

This gas was compressed in the compressor 4 from 26 to 66 bars and was then fed to the methanol synthesis unit 5. The reaction to form methanol was effected in a tubular reactor, which comprised 188 tubes and had a length of 3 meters. The pressure was 64 bars and the temperature 255° C. The gas was passed at a rate of 15 standard $m^3$ per second over a methanol catalyst of type GL 155 which contained copper, zinc, and vanadium. In the methanol synthesis unit 527 kg methanol were produced as well as 726 standard $m^3$ residual gas having the following composition in % by volume:

$CO_2$ — 7.2; CO—9.8;
$H_2$ — 55.6;
$CH_4$ — 25.8;
$N_2$ — 1.6.

205 standard $m^3$ of this residual gas were withdrawn and burnt to produce the heat required for cracking the residual gas.

The remaining 521 standard $m^3$ of the gas were mixed in 6 with 782 standard $m^3$ water vapor and were cracked at 815° C under a pressure of 23 bars, in contact with a nickel-containing steam reforming catalyst of type C11-9 (CCI) to form 897 standard $m^3$ gas having the following composition in % by weight:

$CO_2$ — 10.4;
CO — 11.4;
$H_2$ — 73.5;
$CH_4$ — 3.8;
$N_2$ — 0.9.

This gas was admixed to the pure gas between the gas-purifying unit 3 and the compressor 4.

Thus, as seen above, the residual gas stream from the methanol synthesis is divided into two streams, one cracked with water vapor and the other burnt to produce heat, the ratio of the streams being about 5:2.

The resulting 527 kg methanol had a net calorific value of 2,509,890 kcal. Based on the feed coal having 5,266,000 kcal, the calorific efficiency of the conversion was 47.7%.

What is claimed is:

1. A process of producing methanol comprising
   (a) gasifying coal by a counterflow treatment with oxygen and water vapor;
   (b) cooling the resultant gas;
   (c) scrubbing and purifying the resultant gas with cold methanol at a temperature of −40° C;
   (d) in a tubular reaction zone synthesizing methanol at a pressure of about 64 bars, a temperature of about 255° C and in the presence of a catalyst containing copper, zinc and vanadium;
   (e) withdrawing methanol and residual gas from said tubular reaction zone, dividing said residual gas into a first and a second partial stream at a ratio of about 5:2;
   (f) mixing the first partial stream of said residual gas with water vapor and reacting the mixture in contact with a nickel-containing steam reforming catalyst at a pressure of about 10–30 bars and at a temperature of about 700–850° C to produce a gas rich in carbon oxides and hydrogen;
   (g) burning the second partial stream of said residual gas for heating the reaction of the first partial stream in step (f), and
   (h) cooling the gas rich in carbon oxides and hydrogen from step (f), mixing it with cooled gas from step (b) or scrubbed and purified gas from step (c) and supplying it to the methanol synthesis of step (d).

* * * * *